(12) United States Patent
Shen et al.

(10) Patent No.: US 10,151,678 B2
(45) Date of Patent: *Dec. 11, 2018

(54) EVALUATING SOLID PARTICLE SEPARATION IN WELLBORE FLUIDS

(71) Applicant: Halliburton Energy Services, Inc., Houston, TX (US)

(72) Inventors: Rui Shen, Humble, TX (US); Timothy N. Harvey, Humble, TX (US); Dale E. Jamison, Humble, TX (US); Cato Russell McDaniel, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,027

(22) PCT Filed: Nov. 25, 2014

(86) PCT No.: PCT/US2014/067368
§ 371 (c)(1),
(2) Date: Dec. 16, 2015

(87) PCT Pub. No.: WO2016/085472
PCT Pub. Date: Jun. 2, 2016

(65) Prior Publication Data
US 2017/0254735 A1  Sep. 7, 2017

(51) Int. Cl.
*G01N 15/06* (2006.01)
*G01N 21/51* (2006.01)
(Continued)

(52) U.S. Cl.
CPC ......... *G01N 15/0631* (2013.01); *G01B 11/06* (2013.01); *G01N 15/06* (2013.01);
(Continued)

(58) Field of Classification Search
CPC .. G01N 15/0631; G01N 21/51; G01N 15/082; G01N 2021/4709; G01N 21/532;
(Continued)

(56) References Cited

U.S. PATENT DOCUMENTS 3,204,449 A * 9/1965 Fordyce ............... G01N 15/082
                                                        73/38
3,354,772 A * 11/1967 Topol ................... G01N 21/274
                                                       250/564

(Continued)

FOREIGN PATENT DOCUMENTS

WO        2014062670 A1    4/2014

OTHER PUBLICATIONS

International Search Report and Written Opinion for International Application No. PCT/US2014/067368 dated Aug. 7, 2015.

(Continued)

*Primary Examiner* — Isiaka Akanbi
(74) *Attorney, Agent, or Firm* — Tenley Krueger Tumey L.L.P.

(57) ABSTRACT

Turbidity measurement systems and methods of using the same are described. A turbidity measurement system comprises a vessel configured to hold a wellbore fluid, wherein a porous media is positioned in the vessel; a light source positioned to direct light at the vessel; a light detector positioned to measure light intensity of light emitted by the light source and passing through the vessel; a backscatter detector configured to measure the light intensity of reflected light emitted from the light source; and a computer system communicatively coupled to at least one of the light source, light detector, or light detector.

10 Claims, 4 Drawing Sheets

(51) Int. Cl.
*G01N 21/53* (2006.01)
*G01B 11/06* (2006.01)
*G01N 15/08* (2006.01)
*G01N 21/47* (2006.01)

(52) U.S. Cl.
CPC ........... *G01N 15/082* (2013.01); *G01N 21/51* (2013.01); *G01N 21/532* (2013.01); *G01N 2015/0693* (2013.01); *G01N 2015/084* (2013.01); *G01N 2021/4709* (2013.01); *G01N 2201/061* (2013.01)

(58) Field of Classification Search
CPC ...... G01N 21/253; G01N 21/85; G01B 11/06; E21B 47/102
USPC .......................... 356/342, 335–336, 445, 343
See application file for complete search history.

(56) References Cited

U.S. PATENT DOCUMENTS

| 3,713,743 | A | | 1/1973 | Simms | |
|---|---|---|---|---|---|
| 5,591,975 | A | * | 1/1997 | Jack | G01N 21/3504 250/338.5 |
| 6,795,183 | B2 | * | 9/2004 | O'Keeffe | G01N 15/0205 356/338 |
| 2004/0118558 | A1 | | 6/2004 | Rial et al. | |
| 2010/0182591 | A1 | * | 7/2010 | Chambon | G01N 15/0618 356/51 |
| 2014/0166361 | A1 | * | 6/2014 | Jamison | E21B 21/065 175/24 |
| 2014/0166871 | A1 | | 6/2014 | Jamison et al. | |
| 2016/0370287 | A1 | * | 12/2016 | Barnes | G01N 21/05 |

OTHER PUBLICATIONS

EPA Guidance Manual, Turbidity Provisions, 1999, internal pp. 11(1)-11(13).
AIChE Journal, 2007, vol. 53, Iss. 9, pp. 2275-2283.
In: SPE Int. Symposium on Oilfield Chem., Soc. of Petroleum Engineers, 1993, internal pp. 1-10.

* cited by examiner

EVALUATING SOLID PARTICLE SEPARATION IN WELLBORE FLUIDS

BACKGROUND

Embodiments are directed to methods and systems for evaluating the solid particle separation of wellbore fluids, and more particularly, embodiments disclose using turbidimetry to measure the separation of solids from wellbore fluids as the wellbore fluids flow across porous media.

Solid removal processes and solids control systems may be an important aspect of wellbore fluid treatment. For example, the removal of solids from drilling fluids may be important to maintain the integrity of the fluid. If solids are not sufficiently removed from the drilling fluid, the amount of drilling fluid that may be reused may be reduced, resulting in additional operations expenditures. Further, higher than normal concentrations of solids in wellbore fluids may require additional amounts of said wellbore fluids to dilute the solids so that they do not impact wellbore operations. The need for additional amounts of wellbore fluids may also result in additional operations expenditures.

For fine suspended solids, which may be too small for separation with gravitational or centrifugal methods, a barrier method such as a filter may be used for solids removal. When using a filter, a filter cake, with increasing thickness, may be formed on the face of the filter over time. Generally, the removal of solids or the formation of a filter cake may be measured through the monitoring of the pressure-flow characteristics of the wellbore fluid. However, this evaluation requires may require calculation and calibration of the pressure and flow rate, and thus the dynamics of filter cake formation cannot be studied directly. Further, gathering feedback from this process to alter upstream and downstream operations may require more additional time and, thus, additional expense. Additionally, the above methods may be subject to uncontrollable variables that may distort estimates and calculations and lead to incorrect regulation of upstream and downstream operations.

BRIEF DESCRIPTION OF THE DRAWINGS

These drawings illustrate certain aspects of some of the embodiments of the present invention, and should not be used to limit or define the invention.

DETAILED DESCRIPTION

Embodiments are directed to methods and systems for evaluating the solid particle separation of wellbore fluids, and more particularly, embodiments disclose using turbidimetry to measure the separation of solids from wellbore fluids as the wellbore fluids flow across porous media.

Generally, the methods and systems disclosed herein may comprise one or more turbidity measurement apparatuses. Turbidity measurement apparatuses, also commonly referred to as turbimeters or more generally as nephelometers, may be used to measure the turbidity of a liquid. These apparatuses may pass a known wavelength of light through a wellbore fluid and then may measure the intensity of the transmitted light as well as the light backscattered by the wellbore fluid. This process ultimately produces a measurement of the absorbed light that can be used to determine the turbidity level of the wellbore fluid. The turbidity of the wellbore fluid may be correlated with the amount of suspended solids in the wellbore fluid. As such, this analysis may allow for the study of the dynamics of the suspended solids in the wellbore fluid.

The turbidity measurement apparatus may generally comprise a light emitter and a light detector. Further, the methods and systems may additionally utilize a wellbore fluid. The wellbore fluid may be a sample from any such wellbore fluid for use in a wellbore. The wellbore fluid may additionally comprise suspended solids. Generally, the suspended solids in the wellbore fluid may be measured by the turbidity measurement apparatus. The wellbore fluid may be placed into a vessel containing a porous media, such as a filter. Pressure may be applied to force the wellbore fluid across the porous media. Solids from the wellbore fluid may be filtered by the porous media and can form a filter cake on the face thereof. The measurements of the suspended solids in the wellbore fluid and/or filter cake may be used to analyze the effectiveness of the porous media.

Figure 1:
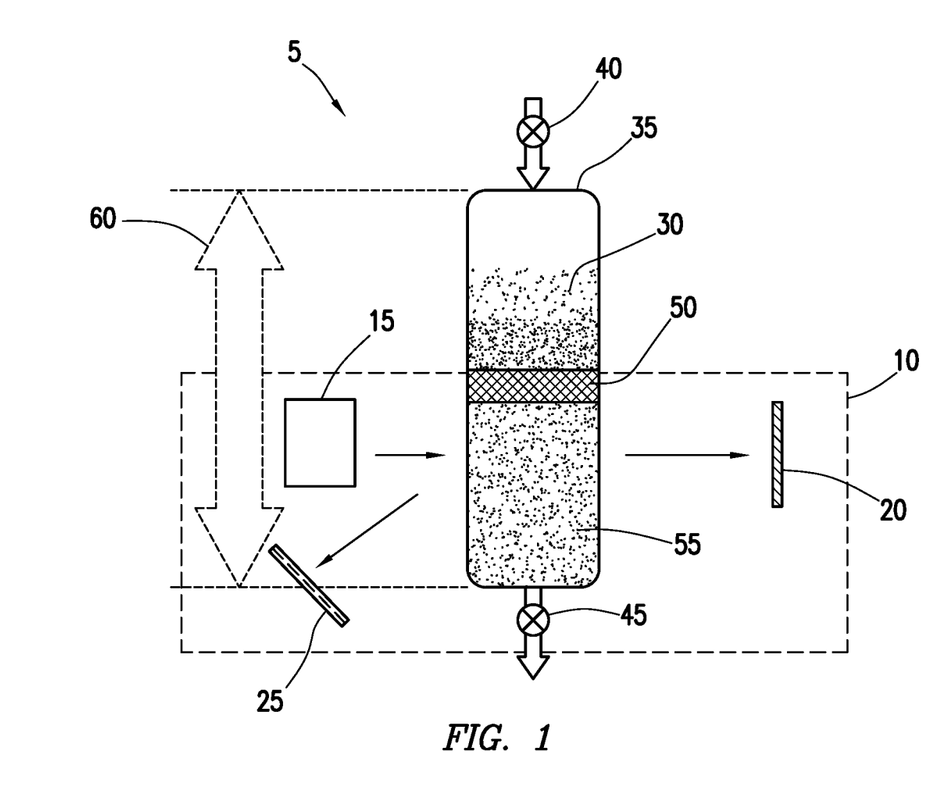
FIG. 1 is an illustration depicting an example turbidity measurement system used to measure the effectiveness of a filtration process.

FIG. 1 is an illustration depicting an example turbidity measurement system 5 used to measure the effectiveness of a filtration process. Turbidity measurement system 5 may comprise a turbidity measurement apparatus 10, which, for ease of illustration is generally illustrated as a collective of its component parts. Turbidity measurement apparatus 10 may generally comprise a light source 15 and a light detector 20. Optionally, turbidity measurement apparatus 10 may also comprise a backscatter detector 25. Turbidity measurement apparatus 10 may comprise a single unit wherein all of the component pieces or disposed within or about the single unit. Alternatively, turbidity measurement apparatus 10 may be formed from individual modules comprising one or more of the components of turbidity measurement apparatus 10 that are connected in a manner sufficient to form a functioning turbidity measurement apparatus 10.

Light source 15 may be any such light source sufficient for use with turbidity measurement apparatus 10. Light source 15 is not to be restricted to the emission of visible light, but may also emit any suitable wavelength of electromagnetic radiation including full spectrum light, infrared, ultraviolet light A, ultraviolet light B, ultraviolet light C, etc. For example, light source 15 may emit light of a wavelength in a range of 600 nm to 1000 nm. Light source 15 may comprise any source of light including, without limitation, filaments, bulbs, lasers, fiber optics, light emitting diodes, and the like. Light source 15 may optionally comprise a filter (not shown) to select for a specific wavelength of light. Turbidity measurement apparatus 10 may comprise more than one light source 15, and light source(s) 15 may be positioned at any desirable angle. With the benefit of this disclosure, one having ordinary skill in the art will be able to select a suitable light source for use with the methods and systems disclosed herein.

Light detector 20 and backscatter detector 25 may be any light detectors sufficient for use with turbidity measurement apparatus 10. As used herein, light detector 20 describes a light detector that measures the intensity of light transmitted from the light source 15 through a wellbore fluid to light detector 20. Whereas backscatter detector 25, as used herein, describes a light detector that measures the intensity of the light reflected from reflective particles in a wellbore fluid as light source 15 transmits light through the wellbore fluid. Thus, the difference between light detector 20 and backscatter detector 25 is a matter of the positioning of the detectors. Light detector 20 and backscatter detector 25 may comprise the same type of light detector or may comprise different types of light detectors. Without limitation, examples of light detectors may include radiometers, photometers, photodetectors, photonic detectors, photovoltaics, photoconductive detectors, phototransistors, photodiodes, and the like. Turbidity measurement apparatus 10 may comprise more than one light detector 20 and/or backscatter detector 25. Light detector 20 and backscatter detector 25 may be positioned at any desirable angle, with the caveat that the positioning of light detector 20 and backscatter detector 25 must be relative to light source 15 so that any light detector 20 and backscatter detector 25 may be able to adequately detect and measure the intensity of the light emitted by the light source 15. With the benefit of this disclosure, one having ordinary skill in the art will be able to select a suitable light detector and backscatter detector for use with the methods and systems disclosed herein.

With continued reference to FIG. 1, turbidity measurement system 5 additionally comprises a wellbore fluid 30. Wellbore fluid 30 may be any such wellbore fluid in which the dynamics of the flow and separation of solids is desirable. Without limitation, examples of wellbore fluid 30 include drilling fluids, fracturing fluids, lost circulation fluids, displacement fluids, drill-in fluids, and any type of treatment fluid. Wellbore fluid 30 may comprise solids. The solids may be any such solids found in a wellbore or introduced into a wellbore fluid. Without limitation, examples of solids include, pieces of the formation, drill cuttings, and additives introduced to a wellbore fluid, e.g., lost circulation materials, proppants, etc. The solids may comprise any such particle size and shape. Of particular relevance may be solids that are too small for gravitational or centrifugal separation methods. Some of the solids suspended in wellbore fluid 30 may reflect light emitted by light source 15. The reflected light may be detected and measured by one or more backscatter detectors 25. With the benefit of this disclosure, one having ordinary skill in the art will be able to recognize suitable wellbore fluids for use with the methods and systems disclosed herein.

FIG. 1 further depicts the injection of wellbore fluid 30 into a vessel 35. Vessel 35 may be any such vessel suitable for containing wellbore fluid 30 and for allowing light emitted from light source 15 to pass through. Because light detector 20 and backscatter detector 25 measure the intensity of light passing through or reflected by solids within wellbore fluid 30, it is important that vessel 35 containing wellbore fluid 30 not diminish or otherwise alter the intensity of the light to be measured. Thus, preferred embodiments of vessel 35 comprise materials that are transparent or nearly transparent and that have little to no reflective characteristics. Examples of materials may include, but should not be limited to, glass or transparent plastics, for example, acrylic. Vessel 35 may be any size and shape, for example vessel 35 may be a cylinder, cubic, etc. Vessel 35 may comprise an injection port 40 and a filtrate port 45. Injection port 40 may comprise any type of port sufficient for allowing wellbore fluid 30 to be introduced to the interior of vessel 35. Filtrate port 45 may comprise any type of port sufficient allowing the filtrate of wellbore fluid 30 to exit the interior of vessel 35. With the benefit of this disclosure, one having ordinary skill in the art will be able to select a suitable vessel for use with the methods and systems disclosed herein.

Within vessel 35, filter 50 may be disposed. Filter 50 may be any such filter used to remove solids from wellbore fluid 30. As discussed above, after wellbore fluid 30 is passed through filter 50, the filtrate 55 of wellbore fluid 30 may exit vessel 35 via filtrate port 45. The filtrate 55 of wellbore fluid 30 may comprise fewer solids than wellbore fluid 30. Filter 50 may be a filter used with a high-pressure, high-temperature filtration system. Filter 50 may have any desired porosity. Pressure may be applied to wellbore fluid 30 in order to force wellbore fluid 30 through filter 50. Alternatively, no pressure may be applied to wellbore fluid 30 and the gravitational pull on wellbore fluid 30 may be sole method of passing wellbore fluid 30 through filter 50. A commercial example of filter 50 is the Series 300 API Low Pressure Low Temperature (LPLT) Filter Press, available from Fann® Instrument Company, Houston, Tex. Working pressure of this system is 100 psig and the filtering area is 7.1-in$^2$, as specified in the American Petroleum Institute, API Recommended Practice 13B-1 and 13B-2. An example of the filter is the filter paper recommended by API 13B-2. With the benefit of this disclosure, one having ordinary skill in the art will be able to select a suitable filter for use with the methods and systems disclosed herein.

With continued reference to FIG. 1, turbidity measurement apparatus 10 may measure the filtration efficiency of filter 50 by measuring the intensity of the light passing through wellbore fluid 30 as well as the intensity of the light reflected by any solids within wellbore fluid 30. The data obtained from this measurement may show the amount that the light emitted by light source 15 is diminished by reflection due to the presence of solids suspended in wellbore fluid 30. Thus, the reduction in light intensity data may be used to determine the turbidity of the wellbore fluid 30. The data may be particularly beneficial, for example, to analyze and detect fine particles (e.g., particle size of from 1 nm to 10 mm) in the wellbore fluid 30. This turbidity measurement may be compared with a second turbidity measurement obtained by measuring intensity of the light passing through the filtrate 55 of wellbore fluid 30 as well as the intensity of the light reflected by any solids within the filtrate 55 of wellbore fluid 30. By comparison of the turbidity level of the wellbore fluid 30 prior to filtration by filter 50 with the turbidity level of the filtrate 55 of wellbore fluid 30, the effectiveness of filter 50 at reducing the turbidity level and thus the amount of solids suspended in wellbore fluid 30 may be deduced. The above description describes a simplified view of the overall process where only measurement on either side of the filer 50 is obtained. However, the turbidity measurement apparatus 10 may scan a portion of, or the entirety of the length and/or width of the vessel 35 as illustrated by arrow 56 and then use the measurements of the scan to capture the filtration efficiency of filter 50 in real time. This method may comprise taking multiple measurements of wellbore fluid 30 and filtrate 55. Further, the scan of the length and/or width of the vessel 35 may be continuous so that turbidity measurement apparatus 10 continuously scans the length and/or width of the vessel 35 providing real time updates of the efficiency of filter 50 over time. Lastly, the entire process may be a continuous flow process or may be a batch process. In a continuous flow process, wellbore fluid 30 may be continuously injected via injection port 40 into vessel 35 and may be continuously scanned by turbidity measurement apparatus 10 as it enters vessel 35, passes through filter 50, and exits vessel 35 via filtrate port 45. Thus, turbidity measurement apparatus 10 is able to obtain real time measurements of wellbore fluid 30 as it is continuously filtered by filter 50. Such measurements may be important for determining whether a wellbore fluid 30 may be reused or whether a wellbore fluid 30 needs to be diluted. A batch process does not use continuous flow injection of wellbore fluid 30, but may use continuous scanning by turbidity measurement apparatus 10. In a batch process example, a set amount of wellbore fluid 30 is injected into vessel 35 and measured by turbidity measurement apparatus 10. Measurements obtained from a batch process may be important for determining the experimental effectiveness of a filter prior to use in the field.

Figure 2:
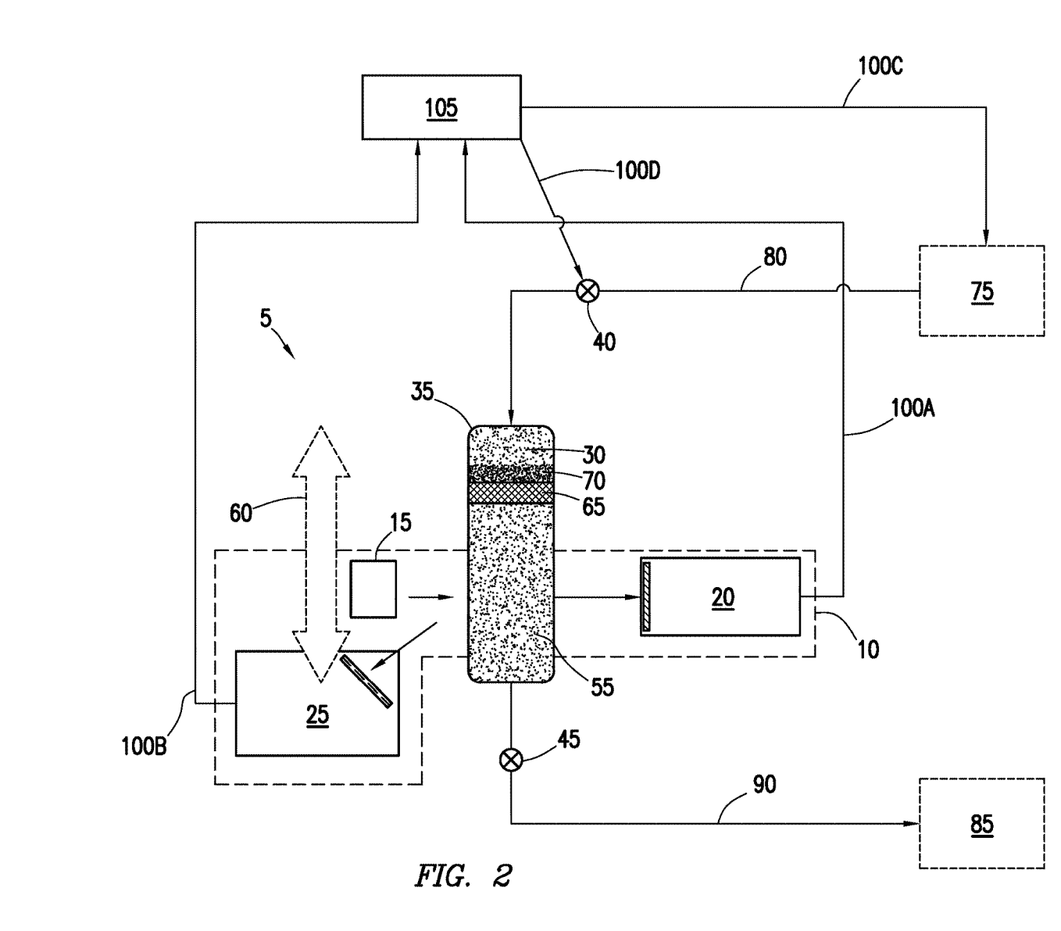
FIG. 2 is an illustration depicting an example turbidity measurement system that may be used in the field to test the dynamics of filter cake formation in a subterranean formation.

FIG. 2 is an illustration depicting an example turbidity measurement system 5 that may be used in the field to test the dynamics of filter cake formation in a subterranean formation. As with FIG. 1, the turbidity measurement system 5 may comprise a turbidity measurement apparatus 10 which may comprise a light source 15, a light detector 20, and backscatter detector 25. Turbidity measurement system 5 may also comprise a vessel 35 with injection port 40 and filtrate port 45. FIG. 2 further comprises a porous media 65. The porous media 65 may be any porous media. For example, porous media 65 may be a filter 50 (e.g., FIG. 1) designed to mimic the filtering properties of a subterranean formation of interest or the porous media 65 may be a cross section of the subterranean formation of interest. Moreover, the example contemplates embodiments that do not use wellbore fluids, for example, the turbidity measuring system 5 may be used to remove solids during drug production, to analyze the purity of beverages, etc. In these applications, porous media 65 may be any such filter suitable for use with those applications.

In the method described by the example of FIG. 2, the dynamics of filter cake 65 formation may be an area of particular interest. Filter cake 70 is the residue that forms at the interface between the wellbore fluid 30 and the porous media 65. As wellbore fluid 30 passes through porous media 65, solids suspended in wellbore fluid 30 that are too large, or are otherwise incapable of passing through porous media 65, may deposit on the surface of porous media 65. The residue formed from this solid deposition is the filter cake 70. There are many variables that may affect the formation of a filter cake including the amount of contact a wellbore fluid has with a formation, the pressure of the system, the type of subterranean formation, the solids volume fraction of the wellbore fluid, the chemical and physical properties of the wellbore fluid, and the chemical and physical properties of the subterranean formation. The dynamics in which these properties affect the formation of filter cake 70 may be analyzed by turbidity measurement system 5.

With continued reference to FIG. 2, the example turbidity measurement system 5 may be further connected to upstream process 75 and downstream processes 85. Upstream process 75 may be any such process that occurs upstream of the use of the turbidity measurement apparatus 10. For example, upstream process 75 may include the preparation of wellbore fluid 30, the addition of additives to wellbore fluid 30, the removal of larger suspended solids such as drill cuttings by centrifuges and/or vibrating screens, and the like. The upstream process 75 may comprise a separation process that removes larger solids from the wellbore fluid 30. For example, a hydroclone may remove solids having a particle size of greater than 10 microns. The size of the solids to be removed is dependent upon the mechanical design of the system. After completion of any upstream process 75, the wellbore fluid 30 may be pumped to injection port 40 via upstream piping 80.

Continuing with FIG. 2, wellbore fluid 30 may be injected into the interior of vessel 35 via injection port 40. Wellbore fluid 30 may be injected into vessel 35 under pressure. The pressure used may be similar to or the same as the wellbore pressure if desired. As wellbore fluid 30 enters the interior of vessel 35, at least a portion of wellbore fluid 30 may begin to flow through porous media 65 and then out of vessel 35 via filtrate port 45. If wellbore fluid 30 comprises suspended solids, a portion of said suspended solids may deposit at the interface of wellbore fluid 30 and porous media 65 forming filter cake 70. Turbidity measurement apparatus 10 may continuously scan a portion of, or the entirety of the length and/or width of the vessel 35 as illustrated by arrow 60 providing real time updates of the dynamics of the suspended solids present in the wellbore fluid 30 over time. In a continuous flow process, the turbidity measurement of the wellbore fluid 30 may increase over time should the thickness and density of the filter cake 70 increase. Alternatively, should the interaction between the porous media 60 and the wellbore fluid 30 not allow for sufficient filter cake 70 formation, the relative amount of turbidity in the wellbore fluid 30 may remain close to constant. As such, the overall values describing the permeability and porosity of the porous media 65 and the filter cake 70 may be studied in real time as the porous media 60 interacts with wellbore fluid 30. Additionally, the thickness and density of the filter cake 70 may be directly measured without the need for calculation or calibration using pressure and flow measurements. Further, the variables of filter cake 70 formation that were discussed above, e.g., pressure of the system, amount of contact, etc., may be altered to further study the dynamics of the filter cake 70 formation process if desired. Additionally, if a filter 50 (e.g., FIG. 1) was deployed as porous media 65, the filter 50 performance may be monitored and adjusted if desired.

As turbidity measurement apparatus 10 scans a portion of, or the entirety of the length and/or width of the vessel 35 as illustrated by arrow 60, turbidity measurement apparatus 10 may also scan the filtrate 55. Turbidity analysis of the filtrate 55 may allow for analysis of changes in the solids content of the filtrate 55 over time. This information may be important for determining whether the filtrate 55 is suitable for downstream processes 85. Filtrate 55 may exit vessel 35 via filtrate port 45 where it may be pumped via downstream piping 90 to any such downstream processes 85. Downstream processes 85 may include any processes downstream of turbidity measurement apparatus 10, for example, recycling of filtrate 55, reuse of filtrate 55 to prepare new wellbore fluid 30, storage of filtrate 55 for later use, or further separation processes, and the like. As mentioned above, analysis of the solids content of filtrate 55 may be important for determining whether filtrate 55 requires further filtration and/or dilution before and/or during downstream processes 85.

With further reference to FIG. 2, communication links 100A, 100B, 100C, and 100D may connect computer system 105 to turbidity measurement system 5. Communication link 100A may transmit signal data from light detector 20 to external computer system 105. Communication link 100B may transmit signal data from backscatter detector 25 to external computer system 105. Communication link 100C may transmit signal data from external computer system 105 any upstream processes 75. Communication link 100D may transmit signal data from external computer system 105 to injection port 40.

Figure 3:
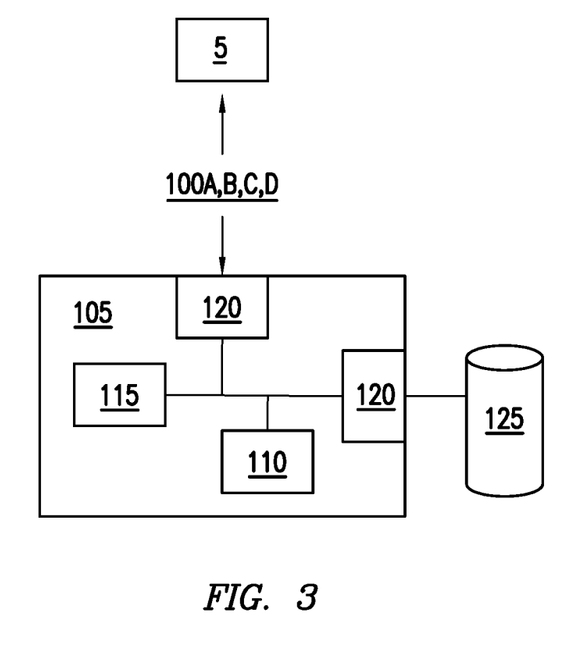
FIG. 3 is an illustration of an example turbidity measurement system communicatively coupled to a computer system.

FIG. 3 further illustrates the connection of the turbidity measurement system 5 to one example of an external computer system 105 via communication links 100A, 100B, 100C, and 100D. Communication links 100A, 100B, 100C, and 100D may include a direct connection, a private network, a virtual private network, a local area network, a WAN (e.g., an Internet-based communication system), a wireless communication system (e.g., a satellite communication system, telephones), combinations thereof, or any other suitable communication link. Computer system 105 may be any suitable data processing system, including computer systems, handheld devices, or any other suitable device. A suitable data processing system may include processor 110, memory 115, and software operable on processor 110 to process and analyze the measurement data generated by turbidity measurement system 5, adjust the parameters of turbidity measurement system 5, and/or operate turbidity measurement system 5. Computer system 105 may comprise a processor 110, memory 115, and input/output ("I/O") interface(s) 120. Processor 110 may comprise one central processing unit or may be distributed across one or more processors in one or more locations. Memory 115 should be communicatively coupled to processor 110. Memory 115 may be read-only memory, random-access memory, or the like. I/O interface(s) 120 should be communicatively coupled to processor 110. I/O interface(s) 120 may be any suitable system for connecting computer system 105 to a communication link, such as a direct connection, a private network, a virtual private network, a local area network, a wide area network ("WAN"), a wireless communication system, or combinations thereof; storage devices, such as storage 125; external devices, such as a keyboard, a monitor, a printer, a voice recognition device, or a mouse; or any other suitable system. Storage 125 may also be provided. Storage 125 may be communicatively coupled to I/O interface(s) 120 or to processor 110. Storage 125 may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for computer system 105.

Data processing and analysis software native to turbidity measurement system 5 and/or installed on computer system 105 may be used to analyze the data generated by turbidity measurement system 5. This procedure may be automated such that the analysis happens without the need for operator input or control. Further, the operator may select from several previously input parameters or may be able to recall previously measured data. Any of the data may be transferable and/or storable on a USB drive if desired. As discussed above, communication links 100A and 100B which may be communicably coupled to light detector 20 and backscatter detector 25 respectively, may be used to transmit signal data from turbidity measurement apparatus 10 to computer system 105. The transmitted data may be analyzed by computer system 105 as discussed above. The analyzed data may be used to optimize upstream operations (e.g., to adjust pressure, temperature, flow rate, etc.) and these adjusted optimization parameters may be transmitted to upstream processes 75 via communication link 100C which communicably couples at least one upstream process 75 to computer system 105. For example, the backscatter detector 25 or the transmission detector 20 may detect an unfavorable light intensity. After the signal has been analyzed by computer system 105, upstream processes, such as the operation pressure of the hydrocyclone separation system, may be adjusted. Further, the data analysis by computer system 105 may also be used to adjust one or more parameters of the wellbore fluid 30, including flow rate into the vessel 35, flow rate out of the vessel 35, solids volume fraction injected into the vessel 35, and pressure. For example, the flow rate of wellbore fluid 30 into the interior of vessel 35 via injection port 40 by regulating the rate of flow through injection port 40. A signal to alter the flow rate through injection port 40 may be transmitted to injection port 40 from computer system 105 via communication link 100D which communicably couples computer system 105 to injection port 40.

Figure 4:
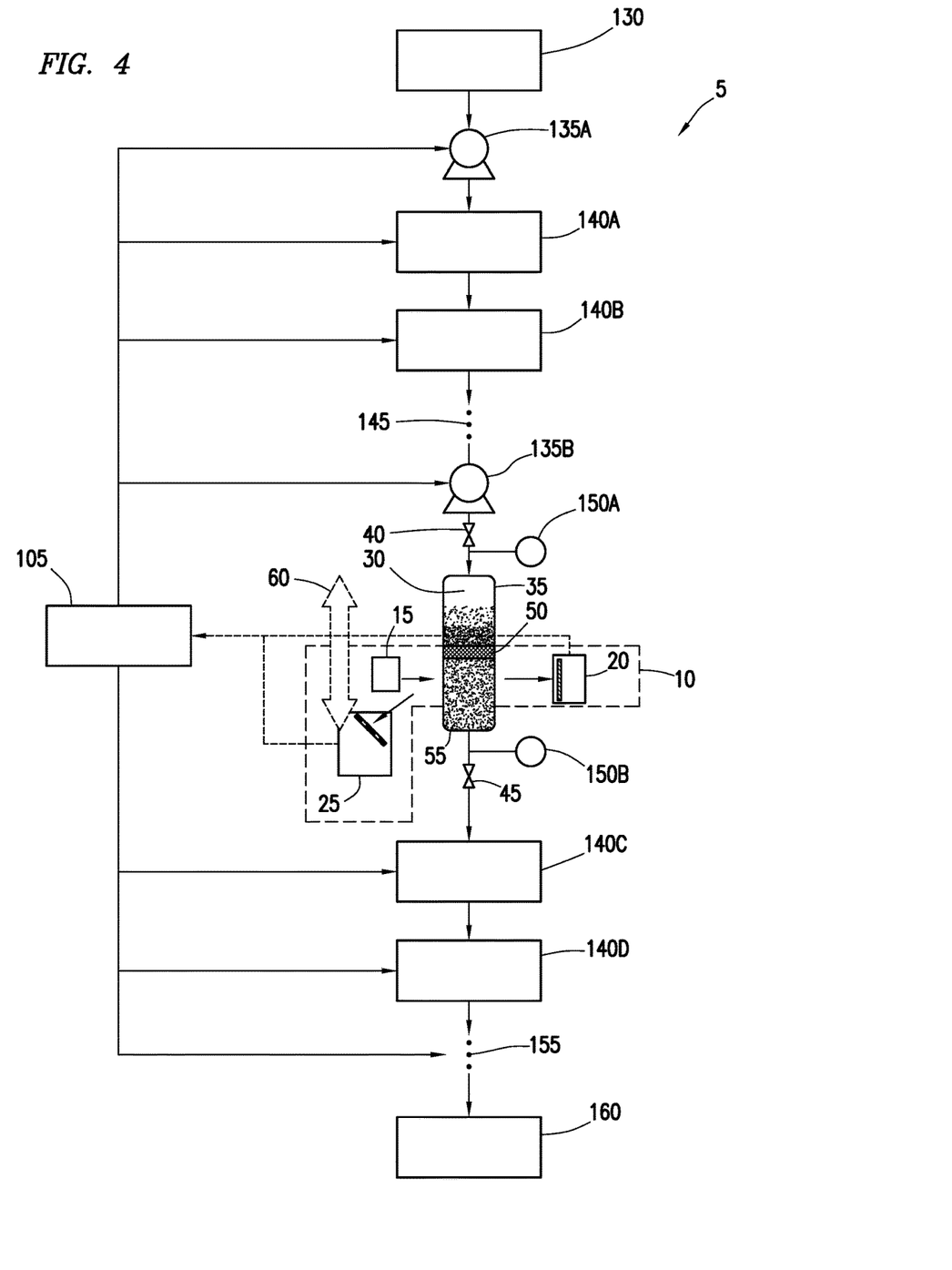
FIG. 4 is an illustration of an example turbidity measurement system which comprises additional components used in the transfer and conditioning of a wellbore fluid.

FIG. 4 illustrates an example turbidity measurement system 5 which comprises additional components used in the transfer and conditioning of wellbore fluid 30. Wellbore fluid 30 may be supplied to turbidity measurement apparatus 10 via wellbore fluid supply 130. Wellbore fluid supply 130 may be any such vessel or conduit used to store and/or transport wellbore fluid 30. Without limitation, examples may include tanks, piping, slurry pits, and the like. Wellbore fluid supply 130 may receive wellbore fluid 30 from any upstream process. Without limitation, examples of upstream processes may include fluid recovery processes or fluid preparation processes. Wellbore fluid 30 may be pumped from wellbore fluid supply 130 by pump 135A. Pump 135A may be any such pump capable of pumping wellbore fluid 30 from wellbore fluid supply 130 or another location to turbidity measurement apparatus 10. Optionally, wellbore fluid 30 may then be transferred to a separator unit 140A. Separator unit 140A may be any such separator unit suitable for separating solids and/or fluids from wellbore fluid 30. Without limitation, examples of separator unit 140A may include screens, filters, hydroclones, shakers, desanders, desilters, centrifuges, and the like. Optionally, after processing by separator unit 140A, wellbore fluid 30 may be pumped to separator unit 140B. Separator unit 140B may be any of the separator units described above. Separator unit 140B and separator unit 140A may be the same type of separator unit or may be a different type of separator unit. Optionally, further separations and/or operations may be done to wellbore fluid 30 at point 145 in the turbidity measurement system 5 if desired. Further, should additional separations and/or operations be used, one or more additional pumps may be required as illustrated by pump 135B. Pump 135B may be the same pump or a different type of pump as compared to pump 135A. Wellbore fluid 30 may then be injected via injection port 40 into vessel 35. Optionally, a temperature measurement sensor 150A may measure the temperature of wellbore fluid 30 prior to or while wellbore fluid 30 is injected into vessel 35. Temperature measurement sensor 150A may comprise any temperature measurement sensor capable of measuring the temperature of wellbore fluid 30.

Once wellbore fluid 30 is injected into vessel 35, the turbidity measurement apparatus 10 may proceed to measure the turbidity of wellbore fluid 30 in any of the manners as described in FIGS. 1 to 3. Once the turbidity measurement apparatus 10 has completed a desired measurement, filtrate 55 may exit vessel 35 via filtrate port 45. Optionally, an additional temperature measurement sensor 150B may measure the temperature of filtrate 55 prior to or after filtrate 55 exits vessel 35 via filtrate port 45.

The measurement data obtained by turbidity measurement apparatus 10 may be sent to a computer system 105 where it may be analyzed and feedback may be derived. As illustrated by FIG. 5, computer system 105 may use the feedback from the turbidity measurement to adjust various aspects of the turbidity measurement system 5 to provide a wellbore fluid 30 with specific properties. Without limitation, some of the aspects that may be adjusted include pumps such as pump 135A and pump 135B; separator units such as separator unit 140A, separator unit 140B, separator unit 140C, and separator unit 140D; and any further upstream or downstream separations and/or operations as noted by points 145 and 155 respectively.

After exiting vessel 35, filtrate 55 may be optionally transferred any downstream separator units such as separator unit 140C and separator unit 140D. Further, if desired, filtrate 55 may undergo additional downstream separations and/or operations as noted at point 155. Once filtrate 55 has been sufficiently conditioned by the above downstream processes, filtrate 55 may be collected in a filtrate collector 160 for use in any additional downstream processes. Filtrate collector 160 may be any such vessel or conduit used to store and/or transport filtrate 55. Without limitation, examples may include tanks, piping, and the like. Additional downstream processes that may use filtrate 55 may include drilling and well treatment processes.

A turbidity measurement system for measuring the turbidity of wellbore fluids may be provided. The turbidity measurement apparatus may include one or of the components illustrated on illustrated on FIGS. 1-4. A turbidity measurement system may comprise a vessel configured to hold a wellbore fluid, wherein a porous media is positioned in the vessel; a light source positioned to direct light at the vessel; a light detector positioned to measure light intensity of light emitted by the light source and passing through the vessel; a backscatter detector configured to measure the light intensity of reflected light emitted from the light source; and a computer system communicatively coupled to at least one of the light source, light detector, or light detector. The light source, light detector, and backscatter detector may be capable of scanning the entirety of the length and/or width of the vessel. The light source, light detector, and backscatter detector may not be connected together as a single unit. The vessel may comprise an injection port and a filtrate port. The porous media may comprise a filter. The computer system may be configured to analyze signal data obtained from the light detector and backscatter detector. The computer system may be configured to adjust an input rate of the wellbore fluid to the vessel in response to the analyzed signal data. The computer system may be configured to adjust one or more parameters of an upstream process in response to the analyzed signal data. The system may further comprise an upstream process coupled to the vessel and configured to deliver the wellbore fluid to the vessel; and a downstream process coupled to the vessel and configured to receive the wellbore fluid from the vessel. The upstream process may comprise a separation process.

A method for measuring the turbidity of wellbore fluids may be provided. The turbidity measurement apparatus may include one or of the components illustrated on illustrated on FIGS. 1-4. A method for measuring the turbidity of a wellbore fluid may comprise injecting a volume of wellbore fluid into the interior of a vessel, wherein a porous media is positioned in the vessel; passing the wellbore fluid through the porous media; measuring the turbidity of the wellbore fluid with a turbidity measurement apparatus, wherein the turbidity measurement apparatus comprises a light source, a light detector, and a backscatter detector; and using the measured turbidity data to determine thickness of a filter cake formed at an interface of the porous media the wellbore fluid. The light source, light detector, and backscatter detector may be capable of scanning the entirety of the length and/or width of the vessel. The light source, light detector, and backscatter detector may not be connected together as a single unit. The porous media may be a filter. The wellbore fluid may be a drilling fluid. The method may further comprise recovering the volume of the wellbore fluid from a wellbore and passing the volume of the wellbore fluid through an upstream process prior to injecting the volume of the wellbore fluid into the interior of the vessel. The computer system may be communicably coupled to the light detector and backscatter detector. The computer system may be used to analyze signal data obtained from the light detector and backscatter detector. The computer system may be used to adjust one or more parameters of the wellbore fluid in response to the measured turbidity data. The porous media may be replaced in response to the measured turbidity data.

The preceding description provides various embodiments of turbidity measurement systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed:

1. A turbidity measurement system comprising:
   a vessel configured to hold the wellbore fluid, wherein the vessel comprises an injection port coupled to a wellbore fluid stream from an upstream process, wherein the vessel comprises a flow path for the wellbore fluid stream, and wherein a porous media is positioned in the vessel;
   a light source positioned to direct light at the vessel;
   a light detector positioned to measure light intensity of light emitted by the light source and passing through the vessel;

a backscatter detector configured to measure the light intensity of reflected light emitted from the light source; and a computer system communicatively coupled to at least one of the light source, light detector, or light detector, wherein the computer system is configured to analyze signal data obtained from at least one of the light detector or the backscatter detector, and wherein the computer system is configured to adjust one or more parameters of the upstream process in response to the analyzed signal data.

2. A system according to claim 1, wherein the light source, light detector, and backscatter detector are capable of scanning the entirety of the length and/or width of the vessel.

3. A system according to any of claim 1, wherein the light source, light detector, and backscatter detector are not connected together as a single unit.

4. A system according to claim 1, wherein the upstream process comprises a separation process.

5. A system according to claim 1, wherein the porous media comprises at least one porous media selected from the group consisting of a filter, a subterranean formation sample, and combinations thereof.

6. A system according to claim 1, wherein the vessel further comprises a filtrate port.

7. A system according to claim 6, wherein the filtrate port is coupled to a downstream process.

8. A method for process control comprising:

receiving a wellbore fluid stream from an upstream process;

injecting a volume of the wellbore fluid into the interior of a vessel, wherein a porous media is positioned in the vessel;

passing the wellbore fluid through the porous media;

measuring the turbidity of the wellbore fluid with a turbidity measurement apparatus, wherein the turbidity measurement apparatus comprises a light source, a light detector, and a backscatter detector, wherein the turbidity measurement apparatus measures a first turbidity of the wellbore fluid before the porous media and a second turbidity of the wellbore fluid after the porous media; and adjusting one or more parameters of the upstream process in response to the first turbidity measurement and the second turbidity measurement.

9. A method according to claim 8, wherein the light source, light detector, and backscatter detector are capable of scanning the entirety of the length and/or width of the vessel.

10. A method according to claim 8, wherein the light source, light detector, and backscatter detector are not connected together as a single unit.

* * * * *